(12) United States Patent
Rudén et al.

(10) Patent No.: US 10,966,878 B2
(45) Date of Patent: Apr. 6, 2021

(54) MALE INCONTINENCE GUARD AND METHOD FOR MANUFACTURING A MALE INCONTINENCE GUARD

(71) Applicant: Essity Hygiene and Health Aktiebolag, Gothenburg (SE)

(72) Inventors: Marcus Rudén, Gothenburg (SE); Peter Rönnberg, Gothenburg (SE); Stina Lindlöf, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 16/618,636

(22) PCT Filed: Jun. 14, 2017

(86) PCT No.: PCT/EP2017/064538
§ 371 (c)(1),
(2) Date: Dec. 2, 2019

(87) PCT Pub. No.: WO2018/228682
PCT Pub. Date: Dec. 20, 2018

(65) Prior Publication Data
US 2020/0179182 A1    Jun. 11, 2020

(51) Int. Cl.
*A61F 13/471* (2006.01)
*A61F 13/15* (2006.01)
(Continued)

(52) U.S. Cl.
CPC ...... *A61F 13/471* (2013.01); *A61F 13/15682* (2013.01); *A61F 13/531* (2013.01);
(Continued)

(58) Field of Classification Search
CPC .................................................. A61F 13/471
See application file for complete search history.

(56) References Cited

U.S. PATENT DOCUMENTS 4,589,877 A * 5/1986 Sivilich ................. A61F 5/4401
                                                                604/385.01
4,627,846 A * 12/1986 Ternstrom ............. A61F 13/471
                                                                604/349
(Continued)

FOREIGN PATENT DOCUMENTS

CN       102939062 A       2/2013
CN       103002850 A       3/2013
(Continued)

OTHER PUBLICATIONS

Office Action (Notification of the First Office Action) dated Nov. 26, 2019, by the State Intellectual Property Office of the Peoples Republic of China in corresponding Chinese Patent Application No. 201780091225.4, and an English Translation of the Office Action. (23 pages).

(Continued)

*Primary Examiner* — Susan S Su
(74) *Attorney, Agent, or Firm* — Buchanan Ingersoll & Rooney P.C.

(57) ABSTRACT

A male incontinence guard having a fluid-impermeable backsheet, a fluid-permeable topsheet facing the user and an absorbent body arranged between the backsheet and the topsheet. The guard has a longitudinal extension along a longitudinal axis and a transverse extension along a transverse axis. The transverse axis divides the guard into an upper region and a lower region. The transverse axis extends between first and second lower corner points which define the two outermost points of the guard, which define a first width. The upper region has an inwardly recessed curvature portion extending between first and second upper corner points. The upper corner points define a second width such that the first width is greater than the second width. The corner points are connected by their respective outer side (Continued)

edges. A method for manufacturing a male incontinence guard is disclosed.

26 Claims, 6 Drawing Sheets (51) Int. Cl.
    *A61F 13/531*     (2006.01)
    *A61F 13/53*     (2006.01)

(52) U.S. Cl.
    CPC ............ *A61F 2013/530481* (2013.01); *A61F 2013/530802* (2013.01); *A61F 2013/530992* (2013.01)

(56) References Cited

U.S. PATENT DOCUMENTS

| | | | |
|---|---|---|---|
| 5,037,417 A | | 8/1991 | Ternstroem et al. |
| 5,702,381 A | * | 12/1997 | Cottenden ............ A61F 13/471 604/349 |
| 6,565,548 B1 | * | 5/2003 | Glaug .................... A61F 5/453 604/349 |
| 10,188,558 B1 | * | 1/2019 | Martin, Sr. .......... A61F 13/4704 |
| 2002/0042600 A1 | * | 4/2002 | Datta .................. A61F 13/5655 604/385.13 |
| 2002/0143316 A1 | * | 10/2002 | Sherrod ................ A61F 13/505 604/385.101 |
| 2004/0059308 A1 | | 3/2004 | Odderson |
| 2007/0060901 A1 | * | 3/2007 | Alletsee ............ A61F 13/47254 604/385.09 |
| 2010/0262111 A1 | * | 10/2010 | Lindstrom ............ A61F 13/471 604/385.03 |
| 2011/0092943 A1 | | 4/2011 | Bishop et al. |
| 2012/0022487 A1 | * | 1/2012 | Akiyama ............. A61F 13/471 604/385.24 |
| 2012/0150134 A1 | | 6/2012 | Wei et al. |
| 2012/0226249 A1 | | 9/2012 | Prodoehl et al. |
| 2013/0030403 A1 | | 1/2013 | Bosaeus |
| 2013/0096525 A1 | | 4/2013 | Hermansson et al. |
| 2013/0138070 A1 | * | 5/2013 | Drevik .................. A61F 13/471 604/385.01 |
| 2013/0218119 A1 | | 8/2013 | Bergendahl |
| 2014/0066875 A1 | | 3/2014 | Hopkins et al. |
| 2015/0126951 A1 | * | 5/2015 | Sharkey ................ A61F 13/471 604/385.03 |
| 2020/0179181 A1 | | 6/2020 | Ruden et al. |
| 2020/0214907 A1 | | 7/2020 | Bremer et al. |

FOREIGN PATENT DOCUMENTS

| | | | | |
|---|---|---|---|---|
| CN | 103491910 B | | 8/2016 | |
| EP | 1035818 A1 | | 9/2000 | |
| EP | 1 105 079 B1 | | 4/2003 | |
| EP | 1 561 444 A1 | | 8/2005 | |
| GB | 2 436 291 A | | 9/2007 | |
| JP | 2003052729 A | | 2/2003 | |
| JP | 2005-230493 A | | 9/2005 | |
| JP | 2010-131342 A | | 6/2010 | |
| JP | 5565920 B1 | * | 8/2014 | ....... A61F 13/15747 |
| KR | 2016004294 U | * | 12/2016 | ........... A61F 13/471 |
| RU | 2430710 C1 | | 10/2011 | |
| RU | 2529109 C2 | | 9/2014 | |
| RU | 2568570 C2 | | 11/2015 | |
| RU | 2606067 C2 | | 1/2017 | |
| RU | 2624435 C2 | | 7/2017 | |
| WO | 8606620 A1 | | 11/1986 | |
| WO | 95/31164 A1 | | 11/1995 | |
| WO | 00/10495 A | | 3/2000 | |
| WO | 2009/067058 A1 | | 5/2009 | |
| WO | 2010071517 A1 | | 6/2010 | |
| WO | 2011037502 A1 | | 3/2011 | |
| WO | 2011/045685 A2 | | 4/2011 | |
| WO | 2011/162658 A1 | | 12/2011 | |

OTHER PUBLICATIONS

Office Action (Decision on Grant) dated May 13, 2020 by the Federal Service for Intellectual Property in Russian Patent Application No. 2019139401/(077480) and an English Translation of the Office Action. (22 pages).

International Search Report and Written Opinion for Internatinal Application No. PCT/EP2017/064538, dated Dec. 4, 2017, 9 pages.

International Preliminary Report on Patentability for International Application No. PCT/EP2017/064538, dated Oct. 2, 2019, 6 pages.

International Search Report and Written Opinion for International Application No. PCT/EP2017/067102, dated Dec. 1, 2017. (8 pages).

Notice of Allowance (Decision to Grant / A Patent for Invention) dated Sep. 10, 2020, by the Federal Service for Intellectual Property in Russian Patent Application No. 2019139673/28(078097) and an English Translation of the Notice of Allowance. (17 pages).

Office Action dated Jun. 4, 2020, by the Federal Service for Intellectual Property in Russian Patent Application No. 2019139673(078097) and an English translation of the Office Action. (21 pages).

Office Action dated Apr. 1, 2020, by the Australian Government/IP Australia in corresponding Australian Patent Application No. 2017422277. (3 pages).

International Preliminary Report on Patentability for International Patent Application No. PCT/EP2017/067092, dated Sep. 5, 2019. (7 pages).

International Search Report and Written Opinion for International Patent Application No. PCT/EP2017/067092, dated Feb. 8, 2018. (10 pages).

Office Action dated Sep. 17, 2020, by the U.S. Patent and Trademark Office in related U.S. Appl. No. 16/618,624. (17 pages).

Office Action (Notification of the Second Office Action) dated Feb. 7, 2021, by the State Intellectual Property Office of the People's Republic of China in corresponding Chinese Patent Application No. 201780091225.4 and an English translation of the Office Action. (26 pages).

\* cited by examiner

MALE INCONTINENCE GUARD AND METHOD FOR MANUFACTURING A MALE INCONTINENCE GUARD

CROSS REFERENCE TO RELATED APPLICATIONS

This is a U.S. National Phase application of PCT/EP2017/064538, filed Jun. 14, 2017, the disclosure of which is incorporated herein by reference in its entirety for all purposes.

TECHNICAL FIELD

The invention relates to a male incontinence guard comprising a fluid-impermeable backsheet, a fluid-permeable topsheet and an absorbent body arranged between said backsheet and said topsheet, wherein said topsheet faces the user when the incontinence guard is worn by said user, said guard having a longitudinal extension along a longitudinal axis and a transverse extension along a transverse axis, said transverse axis dividing said guard into an upper region and a lower region.

The invention also relates to a method for manufacturing a male incontinence guard having a longitudinal extension along a longitudinal axis and a transverse extension along a transverse axis, said transverse axis dividing said guard into an upper region and a lower region. The method comprises: providing a fluid-impermeable backsheet; providing a fluid-permeable topsheet; and providing an absorbent body between said backsheet and said topsheet.

BACKGROUND

Absorbent articles, for example in the form of incontinence guards, baby diapers and sanitary napkins, are well known. The general purpose of such absorbent articles is to absorb, distribute and store various types of body exudates while providing a high level of comfort and sense of dryness to the wearer during use of the absorbent article. Also, such absorbent articles prevent the wearer from getting the clothes soiled by body exudates.

Absorbent articles in the form of incontinence guards are used to protect a wearer against urine leakage. As regards male incontinence guards, such articles are obviously configured for male users and are designed to cover the genital organs so as to protect against unwanted urine leakage. Male persons who are otherwise not physically handicapped will normally prefer not to use an incontinence guard in the form of diaper, since it is considered to be bulky and too large to wear and cannot always be used together with conventional clothing. Instead, special male incontinence guards which are intended for men with light incontinence have been developed. Such incontinence guards are relatively thin and shaped in a manner so as to cover the male genital organs during use. Such incontinence guards can be designed with an absorption capacity which is sufficient in order to absorb the fluid that is expected to be released into the absorbent article when it is worn.

A previously known male incontinence guard of the above-mentioned type is known from the patent document WO 86/06620.

As regards male incontinence guards, there exist certain requirements. Obviously, an incontinence guard should be designed so as to be worn inside a user's ordinary underwear and to provide protection against light urine leakage. For this reason, known male incontinence guards are shaped to provide an optimal fit to the user's undergarment and body. Also, such incontinence guards comprise a core of absorbent material arranged along a longitudinal axis of the product in order to absorb urine.

Furthermore, a male incontinence guard normally comprises a soft topsheet in order to give the wearer a feeling of freshness and dryness. The guard should also be relatively thin and should be designed with a discreet shape so that it is generally not visible through the wearer's regular clothes during use. Finally, it can be provided with suitable adhesive means, allowing it to be attached to the wearer's underwear. The guard also may be easily bent and shaped so as to follow the anatomy of the wearer during use.

Even though the article disclosed in WO 86/06620 fulfills the basic requirement regarding protection against light urine leakage, there is a need for further improvements within this field of technology. Firstly, there is a demand for male incontinence guards of a kind which can be securely fitted and held in place in the undergarments of male persons of different anatomy. In particular, the incontinence guard should, be positioned so that it extends from below the user's belly and downwards so as to cover the genital organs in a secure manner.

Secondly, the incontinence guard should assume a correct, intended shape when it is in place, so as to provide the intended protection against incontinence, even in situations when the user is moving around and when the user is sitting down and standing up. A further requirement is that the incontinence guard should assume a correct, intended shape when it is in place, in order to provide the intended protection against incontinence.

It has been found that known male incontinence guards are not always suited for a correct fitting under the belly of the user and that they not always assume the correct, intended shape when it is in place. This means that optimum incontinence protection is not always guaranteed.

SUMMARY

In accordance with the invention, there is provided a male incontinence guard which is configured so as to solve the above-mentioned problems related to prior art within this field. In particular, the incontinence guard is configured so as to secure an optimal fit for the wearer in its intended position during use.

In accordance with the invention, this object is obtained by means of a male incontinence guard comprising a fluid-impermeable backsheet, a fluid-permeable topsheet and an absorbent body arranged between said backsheet and said topsheet, wherein said topsheet faces the user when the incontinence guard is worn by said user, said guard having a longitudinal extension along a longitudinal axis and a transverse extension along a transverse axis, said transverse axis dividing said guard into an upper region and a lower region. Furthermore, said transverse axis extends between a first lower corner point and a second lower corner point which define two outermost points of said guard between which said guard has a first width; said upper region comprising an inwardly recessed curvature portion extending between a first upper corner point and a second upper corner point and having an arcuate shape, said upper corner points defining a second width; wherein the first width is greater than the second width, and wherein said first lower corner point and first upper corner point and said second lower corner point and second upper corner point, respectively, are connected by outer side edges.

The invention provides certain advantages. Firstly, the invention fulfills the requirements on incontinence guards to be securely fitted and held in place in the undergarments of male persons of different anatomy. In particular, it has been found that the provision of the above-mentioned inwardly recessed curvature portion allows the incontinence guard to be positioned so that it extends from below the user's belly and downwards so as to cover the genital organs in a secure manner. In particular, the geometry of the incontinence guard according to the invention, as defined by means of the above-mentioned upper and lower corner points will provide a secure positioning of the guard even when the user is sitting down and standing up repeatedly, while at the same time providing the intended protection against incontinence.

According to an embodiment, the incontinence guard is formed with a tapering shape as regarded from the lower corner points and along the lower region. This makes it possible to position the guard in a correct manner over the male genital organs during use.

According to a further embodiment, the inwardly recessed curvature portion as mentioned defines an outer boundary edge which extends between said upper corner points and wherein said outer boundary edge lies inwardly of an imaginary transverse line extending between said upper corner points. The outer boundary edge has a radius which is in the range of 60-1400 mm.

Also, the relationship between the first width and the second width is in the range of 30-80%. According to an embodiment, the first width is in the range of 110-280 mm. Also, the second width is in the range of 50-151 mm.

Furthermore, according to an embodiment, the ratio between a distance defined by an imaginary longitudinal line, being parallel to said longitudinal axis and extending from any one of said upper corner points to said transversal axis, and a distance extending from any one of said lower corner points to said longitudinal line, is in the range of 0.25-4.0.

According to a further embodiment, a straight line is defined as extending through a lower corner point and an upper corner point, wherein an angle is defined between said straight line and said imaginary longitudinal line, said angle being in the range of 12-78 degrees.

According to a further embodiment, a measurement is defined as the distance between said straight line and the maximum outer extension of said incontinence guard, said measurement being in the range of 2-10 mm, or wherein said measurement is less than 25% of the distance between first lower corner point and the first upper corner point.

According to a further embodiment, a maximum recess depth d3 of said inwardly recessed curvature portion does not extend below said transversal axis. In an embodiment, said maximum recess depth d3 is preferably in the range of 2-30 mm.

According to an embodiment, the lower region comprises a lower edge having a convex arcuate shape with a radius defining a ratio of 0.9-1.1 to said radius of said inwardly recessed curvature portion.

According to an embodiment, the absorbent body has an outer edge which generally follows the outer edge of the guard and defines an edge region having a width which is generally equal along the entire outer edge of the guard.

Furthermore, according to an embodiment, the absorbent body comprises a primary absorbent core and a secondary absorbent core which arranged in a stacked configuration. In an embodiment, the secondary core preferably has an area in an XY plane which is smaller than an area of the primary core in the XY plane. Also, according to an embodiment, the secondary core is formed with side edges which are at least partly generally parallel to said longitudinal axis. Such an embodiment is advantageous during manufacturing of said incontinence guard, since it allows a precise and efficient folding of each guard during a manufacturing process.

According to an embodiment at least one of said primary core and said secondary core comprises superabsorbent material. According to various embodiments, the superabsorbent material is in the form of a superabsorbent polymer or a foam.

According to a further embodiment, the guard has elasticized elements arranged along an outer edge of the lower region, along the outer edges of said lower region. Such elasticized elements can be in the form of an elasticized film, elastic threads or an elastic foam attached to said guard.

Furthermore, the above-mentioned object of the invention is obtained by means of a method for manufacturing a male incontinence guard having a longitudinal extension along a longitudinal axis and a transverse extension along a transverse axis, said transverse axis dividing the guard into an upper region and a lower region. The method comprises the following steps: providing a fluid-impermeable backsheet; providing a fluid-permeable topsheet; and providing an absorbent body between said backsheet and said topsheet. Furthermore, the method comprises the following steps: folding a first portion of the incontinence guard towards the centre of said incontinence guard; folding a second portion of the incontinence guard towards the centre of said incontinence guard so that it at least partly covers the first portion; and folding a bottom portion upwards so as to partly cover both the first portion and the second portion while forming a distance between a top edge of the incontinence guard and an upper edge of the bottom portion.

Further advantages and advantageous features of the invention are disclosed in the following description and in the dependent claims.

BRIEF DESCRIPTION OF THE DRAWINGS

The invention will be described in greater detail below with reference to the figures shown in the appended drawings.

DETAILED DESCRIPTION OF PARTICULAR EMBODIMENTS

Different aspects of the present disclosure will be described more fully hereinafter with reference to the enclosed drawings. The embodiments disclosed herein can, however, be realized in many different forms and should not be construed as being limited to the aspects set forth herein.

Figure 1:
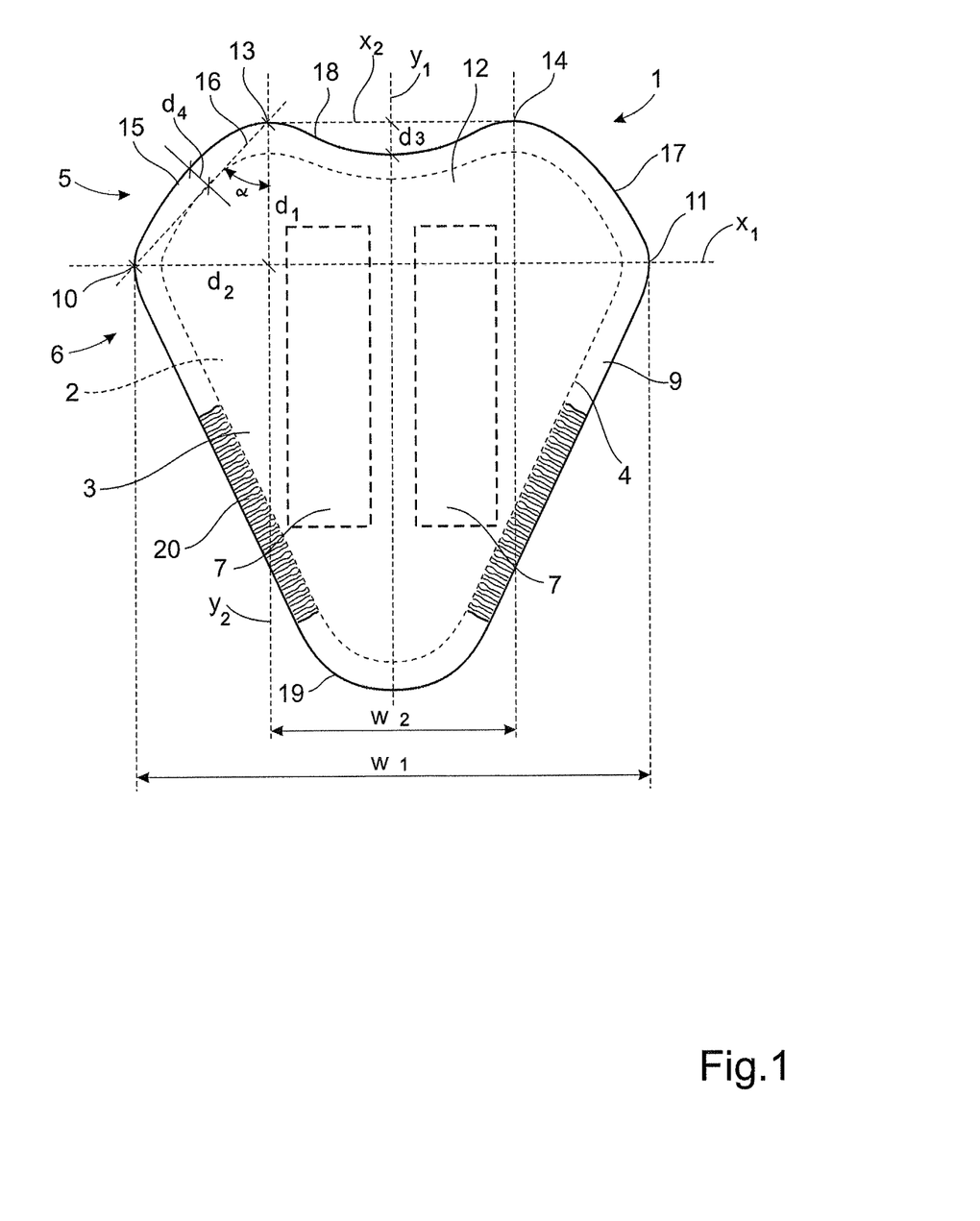
FIG. 1 shows a view from above of a male incontinence guard according to an embodiment of the invention.

With initial reference to FIG. 1, there is shown a view from above of an absorbent article in the form of a male incontinence guard 1 in accordance with an embodiment of the invention. The male incontinence guard 1 is an incontinence protector article which is designed and optimized to absorb light urine leakage for male users. For this reason, and as will be described in detail below, the incontinence guard 1 is based on an absorbent structure for rapidly wicking away urine from the wearer in order to provide a dry, comfortable and odor-free feeling for the wearer.

FIG. 1 shows the incontinence guard 1 in a view from above, from which can be understood that it comprises a fluid impermeable backsheet 2 and a fluid permeable topsheet 3. The incontinence guard 1 also comprises an absorbent core 4 which is sandwiched between the backsheet 2 and the topsheet 3.

The topsheet 3 is arranged at the surface, i.e. the side facing a wearer, of the incontinence guard 1. The backsheet 2 is arranged at the underside of the incontinence guard 1, i.e. facing an undergarment of the wearer. Furthermore, both the backsheet 2 and the topsheet 3 extend laterally outside of the absorbent core 4 along the whole perimeter of the incontinence guard 1. The topsheet 3, backsheet 2 and the absorbent core 4 may consist of any materials suitable for their particular purposes, as will be discussed in further detail below.

According to further embodiments, one or more additional layers may be provided in the incontinence guard 1. For example, an acquisition layer may be arranged between the absorbent core 4 and the topsheet 3.

The above-mentioned layers of the incontinence guard 1 may be connected to each other by any conventional means such as by means of an adhesive, heat bonding or ultrasonic bonding.

As shown in FIG. 1, the incontinence guard 1 has a longitudinal extension along a longitudinal axis Y1 and a transverse extension along a transverse axis X1. The transverse axis X1 divides the incontinence guard 1 into an upper region 5 and a lower region 6, as regarded when being worn by a user. This means that the upper region 5 is intended to be oriented upwards towards the user's belly during use of the incontinence guard 1, whereas the lower region 6 is intended to be facing downwards to cover the genital organs of the wearer during use.

Figure 2:
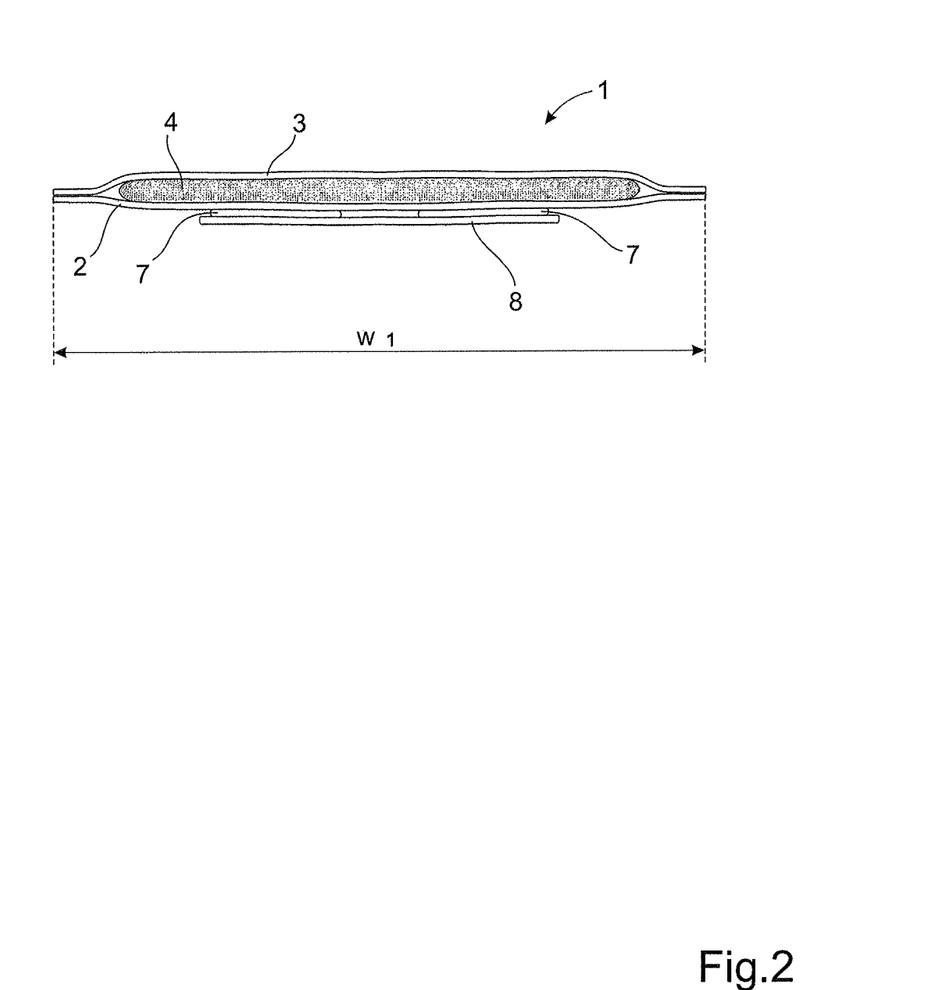
FIG. 2 shows a cross-sectional view of the male incontinence guard, taken along the line II in FIG. 1.

FIG. 2 is a cross-sectional view as taken along transversal axis X1 shown in FIG. 1. The various layers 2, 3, 4 which form part of the incontinence guard 1 will now be described more in detail, with reference primarily to FIGS. 1 and 2.

According to an embodiment, the backsheet 2 is constituted by a fluid-impermeable and breathable layer such as a polymeric film, for example a film of polyethylene or polypropylene. According to different embodiments, the materials which can be used for manufacturing the backsheet 2 include thin and flexible fluid impermeable plastic films, or fluid impermeable nonwoven materials, fluid impermeable foams and fluid impermeable laminates.

According to the embodiment shown in the drawings, the backsheet 2 is formed by a single layer, but can alternatively be formed by a multi-layered structure, i.e. a laminate, wherein at least one layer is fluid impermeable. Furthermore, the backsheet 2 can optionally be elastic in any direction. Also, backsheet materials that are not fully fluid impermeable but only resistant to fluid penetration may be used, particularly in cases where relatively small amounts of urine are expected to be absorbed by the incontinence guard 1. According to further embodiments, the backsheet 2 may be breathable, implying that air and vapor may pass through the backsheet 2. Furthermore, the backsheet 2 may optionally have an outer, garment-facing surface of a textile material such as nonwoven.

Figure 3:
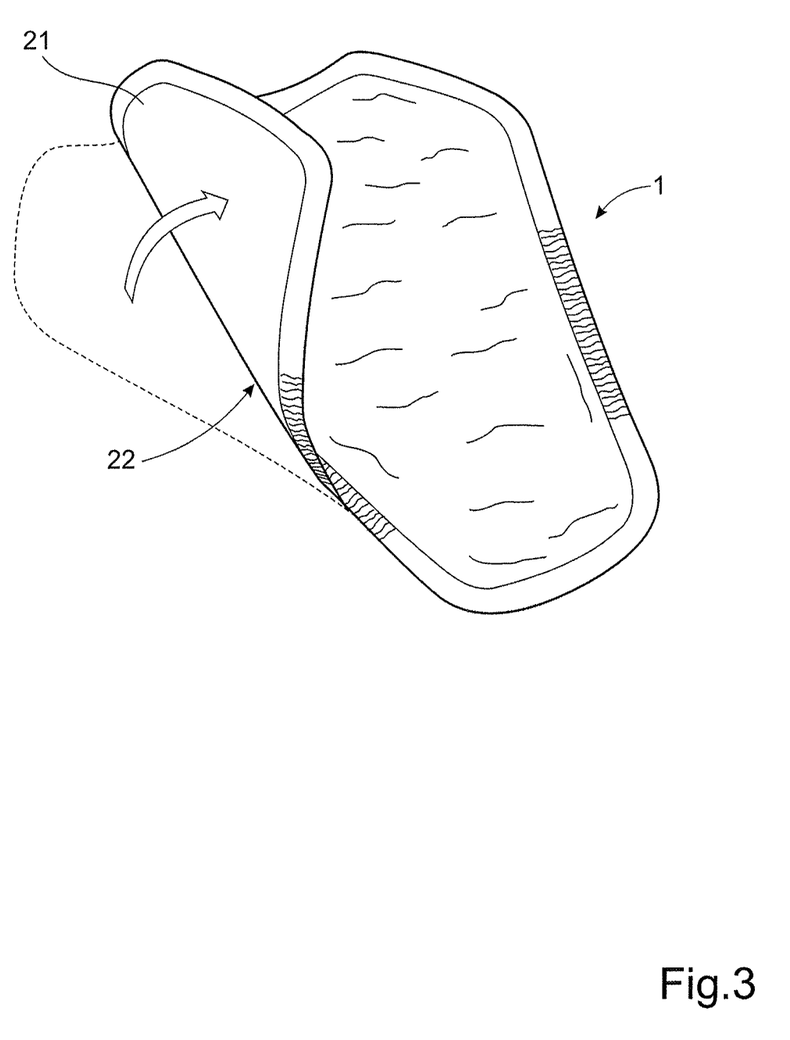
FIG. 3 shows a process for folding the male incontinence guard during a manufacturing process, in a first process step.

Furthermore, the topsheet 3 is according to an embodiment formed by a fluid permeable nonwoven fabric or film which is made of thermoplastic synthetic fibers. The topsheet 3 is sufficiently fluid permeable to allow discharged body fluids such as urine to penetrate through the thickness of the topsheet 3. Also, the topsheet 3 is suitably manufactured from a material which is compliant and soft-feeling to the skin of the wearer.

According to different embodiments, the topsheet 3 may be manufactured from various web materials such as woven and nonwoven webs and films, foams, or combinations of the above-mentioned materials. The nonwoven materials to be used for the topsheet 3 may be for example carded resin bonded materials, carded through-air bonded materials, spunbond-meltbond-spunbond materials, carded hydroentangled materials or carded thermobonded materials. The topsheet 3 may also have elastic properties which allow it to be stretchable.

According to an additional embodiment, the topsheet 3 may be in the form of a perforated plastic film which then serves as a liquid-permeable sheet.

As indicated in FIGS. 1 and 2, the rear side of the backsheet 2 is provided with fastening means for fastening the incontinence guard 1 inside an undergarment (not shown). The fastening means may be in the form of one or several adhesive sections 7 which are arranged on the rear side of the backsheet 2 and which are arranged to extend in a manner which is parallel or non-parallel in relation to the longitudinal axis Y1. As shown in FIG. 2, the adhesive sections 7 are covered with a release paper layer 8 when the incontinence guard 1 is in its non-used condition. When the guard 1 is to be used, the release paper layer 8 is removed by the user so that the guard 1 can be fastened to the undergarment.

According to alternative embodiments, the incontinence guard 1 can be provided with various types of fastening means in the form of frictional fasteners, mechanical fasteners such as the hook-and-loop fastener type or combinations of different types of fasteners, as known in the art.

Furthermore, according to the embodiment shown in FIGS. 1 and 2, the incontinence guard 1 comprises an absorbent core 4 which is formed by one or more layers comprising fibres of cellulosic fluff pulp. According to alternative embodiments, the absorbent core 4 can be made up of any suitable absorbent or fluid-absorbing material as known in the art, for example foam, fiber waddings and similar materials.

According to a further embodiment, the absorbent core 4 comprises a suitable amount of superabsorbent particles. Such superabsorbent material is well known in the field of absorbent articles, and is constituted by a water-swellable and water-insoluble material which is capable of absorbing large quantities of fluid upon formation of a hydrogel. Normal superabsorbent materials are capable of absorbing fluids of at least 10 times its own weight. According to an embodiment, the amount of said superabsorbent particles is at least 10% by weight, i.e. in relation to the total weight of the absorbent core 4.

The superabsorbents are mixed into the material of the absorbent core 4. The absorbent core 4 may further incorporate components for improving the properties of the absorbent core. Some examples of such components are binder fibers, fluid-dispersing materials, fluid acquisition materials, etc. as known in the art. According to an embodiment, a mixture of cellulose fluff pulp and superabsorbent articles is mixed in a generally homogeneous manner throughout the entire absorbent core 4.

According to further embodiments, the absorbent core 1 may be a homogeneous structure or may be a layered structure with laminates of the same or different materials. The absorbent layers may have uniform thickness or may vary in thickness in different parts of the layers. Also, the basis weight and composition of the absorbent core 1 may vary within such absorbent layers.

FIG. 1 shows a view of the side of the incontinence guard 1 that is intended to be facing towards a wearer's body when the incontinence guard 1 is being worn. It can be seen from FIG. 1 that the incontinence guard 1 according to the embodiment has a shape which is generally triangular and which is tapered along its lower region 6. This means that, for instance, the corners and sides of the incontinence guard 1 may be more or less rounded, as shown in FIG. 1.

Furthermore, as mentioned above, the backsheet 2 and the topsheet 3 are connected to each other along an edge region 9 which extends around the perimeter of the incontinence guard 1. The absorbent core 4 is of a size having an area which is slightly smaller than the area of the backsheet 2 and the topsheet 3. According to an embodiment, the edge region 9 has substantially the same width along the entire perimeter of the incontinence guard 1. In other words, the absorbent core 4 is arranged to follow the perimeter of the incontinence guard 1 so that the distance between the outer edge of the absorbent core 4 and the outer edge of the guard 1 remains generally equal along the edge region 9.

The male incontinence guard 1 according to the embodiment shown in FIG. 1 is arranged so that the transverse axis X1 extends between a first lower corner point 10 and a second lower corner point 11. These lower corner points 10, 11 define two outermost points of the incontinence guard 1 along the transverse axis X1. The distance between these lower corner points 10, 11, i.e. the maximum width of the incontinence guard 1, is defined by a first width w1 as indicated in FIG. 1.

Referring to FIG. 1, it should be pointed out that, according to different embodiments, the lower corner points 10, 11 can be constituted by different shape and roundness, for example a softly rounded shape or a more sharply pointed corner shape.

Furthermore, the upper region 5 comprises an inwardly recessed curvature portion 12 which extends between a first upper corner point 13 and a second upper corner point 14. The curvature portion 12 has a generally arcuate shape which extends into the upper region 5. Also, the distance between the upper corner points 13, 14 along the transversal direction is defined by a second width w2.

The first lower corner point 10 and the first upper corner point 13 are connected by a first outer side edge 15 which according to the embodiment has an outwardly and slightly rounded shape. An imaginary straight line 16, which extends through the first lower corner point 10 and the first upper corner point 13, can also be defined. In a similar manner, the second lower corner point 11 and the second upper corner point 14 are connected by a second outer side edge 17 which also has an outwardly and slightly rounded shape. The first and second outer side edges 15, 17 extend outwards as regarded along the direction of the transverse axis X1, i.e. from the upper corner points 13, 14 to the lower corner points 10, 11.

As shown in FIG. 1, the first width w1 is greater than the second width w2, i.e. the lower corner points 10, 11 define the laterally outermost points of the incontinence guard 1.

In summary, the male incontinence guard 1 according to the disclosed embodiment is configured so that the transverse axis X1 extends between the first lower corner point 10 and the second lower corner point 11, which consequently define two laterally extending and outermost points of the guard 1. Between these end points 10, 11, the guard 1 has a first width w1 as seen along the transverse direction. Also, the upper region 5 comprises the inwardly recessed curvature portion 12 which extends between the first upper corner point 13 and the second upper corner point 14. The curvature portion 12 has an arcuate shape in a manner so that the upper corner points 13, 14 define a second width w2 in the transverse direction. As shown in the embodiment of FIG. 1, the first width w1 is greater than the second width w2. Also, the first lower corner point 10 and the first upper corner point 13, and also the second lower corner point 11 and the second upper corner point 14, respectively, are connected by the outer side edges 15, 17. These outer side edges 15, 17 are shown in FIG. 1 as softly rounded edges, but can alternatively also be formed by generally straight edges.

The purpose of the configuration of the incontinence guard 1 shown in FIGS. 1 and 2 is to contribute to its advantageous properties regarding a secure and comfortable fit for the user, while maintaining adequate absorption properties.

The incontinence guard 1 according to the embodiment shown in FIG. 1 is symmetrical with reference to the longitudinal axis Y1. Also, the guard 1 has a tapering shape as regarded from the lower corner points 10, 11 and downwards along the lower region 6. Furthermore, the lower region 6 is according to the embodiment in FIG. 1 formed with generally straight sides. In an alternative embodiment, the sides of the lower region 6 may be convex, i.e. generally without being curved inwards.

According to the embodiment shown in FIG. 1, the above-mentioned inwardly recessed curvature portion 12 defines an outer boundary edge 18 which extends between the two upper corner points 13, 14. The outer boundary edge 18 lies inwardly of an imaginary transverse line X2 which is generally parallel to the transverse axis X1 and extends between the upper corner points 13, 14.

With reference to the embodiment shown in FIGS. 1 and 2, it can be noted that the outer boundary edge 18 has a radius r1 which is in the range of 60-1400 mm, preferably in the range of 120-500 mm.

Also, the ratio between the value of the first width w1 and the value of the second width w2 is in the range of 30-80%, preferably in the range of 40-75%. Regarding the actual measurements of the first width w1 and the second width w2, it can be noted that the first width w1 is in the range of 110-280 mm. Also, the second width (w2) is in the range of 50-151 mm.

Furthermore, according to an embodiment, the ratio between a distance d1 defined by an imaginary longitudinal line Y2 as shown in FIG. 1, and being parallel to the longitudinal axis Y1 and extending from any one of said upper corner points 13, 14 to the transversal axis X1, and a distance d2 extending from any one of said lower corner points 10, 11 to said imaginary longitudinal line Y2, is in the range of 0.25-4.0, preferably in the range of 0.5-2.0.

With further reference to FIG. 1, a straight line 16 can be defined as extending through the first lower corner point 10 and the first upper corner point 13. An angle α can then be defined between said straight line 16 and the above-mentioned imaginary longitudinal line Y2. The angle α is in the range of 12-78 degrees, preferably in the range of 22-68 degrees.

Furthermore, as shown in the drawings, the lower region 6 of the male incontinence guard 1 may comprise a lower edge 19 which has a convex arcuate shape with a radius r2 defining a ratio of 0.9-1.1 to the radius r1 of said inwardly recessed curvature portion 12.

Furthermore, the invention can alternatively be arranged so that the inwardly recessed curvature portion 12 has a geometry which is not equivalent to a circle, i.e. so that it cannot be defined by means of a radius. In such case, a maximum recess depth d3 of the inwardly recessed curvature portion 12 can be defined. According to an embodiment, the curvature portion 12 does not extend below said transversal axis X1. Furthermore, the maximum recess depth d3 is the range of 2-30 mm, preferably in the range of 2-20 mm.

Yet another measurement d4 can be defined as the distance between the above-mentioned straight line 16 extending through the first lower corner point 10 and the first upper corner point 13 and the maximum extension of the upper left corner of the incontinence guard 1, as shown in FIG. 1. According to an embodiment, the distance d4 is in the range of 2-10 mm. Another way of defining this distance d4 is by stating that said distance d4 is less than 25% of the distance between first lower corner point 10 and the first upper corner point 13.

As mentioned above, the male incontinence guard 1 as shown in the drawings is provided with an absorbent body 4 which has an outer edge which generally follows the outer edge of the guard 1. As shown in FIG. 1, the outer edge defines an edge region 9 which has a width which is generally equal along the entire outer edge of the guard 1.

Furthermore, according to the embodiment shown in FIG. 1, the incontinence guard 1 comprises elasticized elements 20 which are arranged along the outer edge 9 of the lower region 6. In an embodiment, the elasticized elements 20 are preferably in the form of an elasticized film which is attached to the incontinence guard 1. According to alternative embodiments, the elasticized elements 20 can be in the form of elastic threads, an elastic foam or an elastic laminate attached to said guard 1.

A process for manufacturing the male incontinence guard 1 described above comprises a number of steps which will now be described. Initially, the absorbent core 4 is sandwiched between the backsheet 2 and the topsheet 3 in a manner which is known as such. Subsequently, the incontinence guard 1 is folded in a manner which will now be described with reference to FIGS. 3, 4 and 5.

Figure 4:
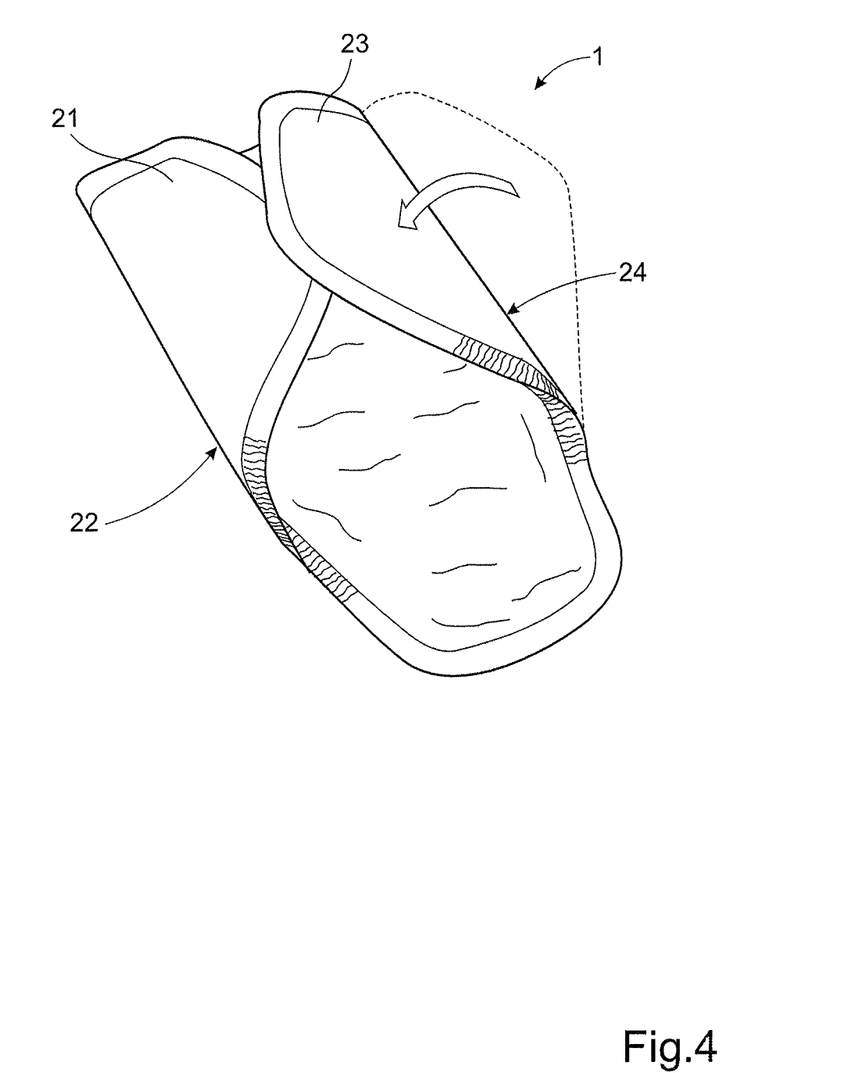
FIG. 4 shows a process for folding the male incontinence guard during a manufacturing process, in a second process step.
Figure 5:
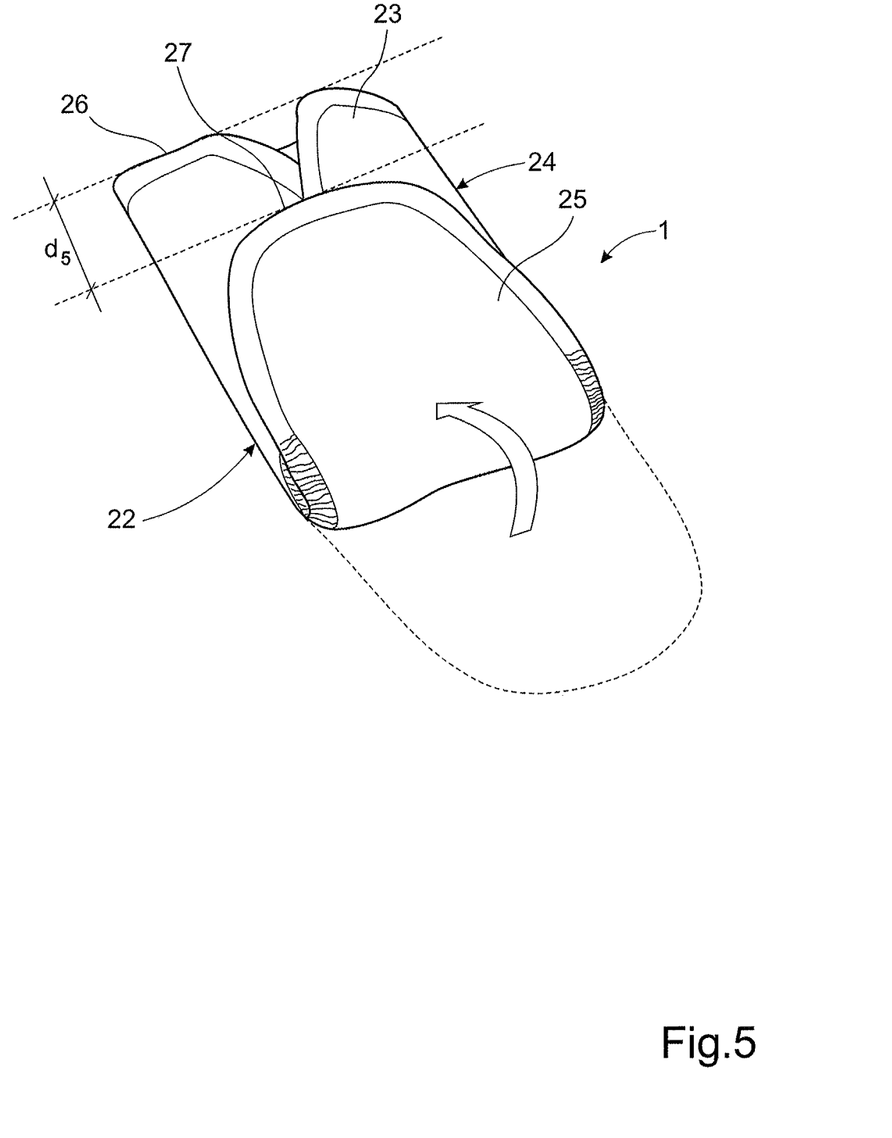
FIG. 5 shows a process for folding the male incontinence guard during a manufacturing process, in a third process step.

Firstly, with reference to FIG. 3, a first (left in the figure) portion 21 of the incontinence guard 1 is folded towards the centre of the guard 1 so that a first fold line 22 is defined extending essentially parallel to the longitudinal centerline y1 and on the first side of the longitudinal centerline. Next, as shown in FIG. 4, a second (right in the figure) portion 23 of the incontinence guard 1 is folded towards the centre of the guard, so that a second fold line 24 is defined, extending essentially parallel to the longitudinal centerline and positioned on the opposite side of the centerline from the first fold line 22, in a manner so as to partly cover an outer part of the left portion 21. Finally, as shown in FIG. 5, a bottom portion 25 is folded upwards along a fold line essentially parallel to the transversal centerline x1 so as to partly cover both the left portion 21 and the right portion 23. During this process, it is also secured that the bottom portion 25 is folded upwards towards the top edge 26 of the incontinence guard 1. There may be a gap formed by the distance between the top edge 26 of the incontinence guard 1 and the edge 27 of the bottom portion 25, as defined by the distance d5 shown in FIG. 5. In folded condition, the top edge 26 may extend beyond the edge 27 of the bottom portion (giving d5 a positive number), as shown in the FIG. 5, or alternatively, the edge 27 of the bottom portion may extend beyond the top edge 26 (not shown in the FIG. 5, giving the d5 a negative value) According to an embodiment, this distance d5 is up to ±30 mm, preferably up to ±10 mm. By folding the incontinence guard 1 as shown in FIGS. 3-5, an advantage is obtained due to the fact that the upper part of the folded incontinence guard 1 will be thinner than the remaining parts of the product, which means that it will be easy for a user to grip the product in a package and to bring it out of the package.

According to an embodiment, preferably, a plurality of incontinence guards 1 are first folded, individually wrapped, suitably in an individual plastic wrapping, and then positioned in a suitable configuration in a packaging unit (not shown in the drawings) such as a plastic or paper bag or box. This configuration corresponds to a plurality of guards 1 folded in a manner such as shown in FIG. 5.

Figure 6:
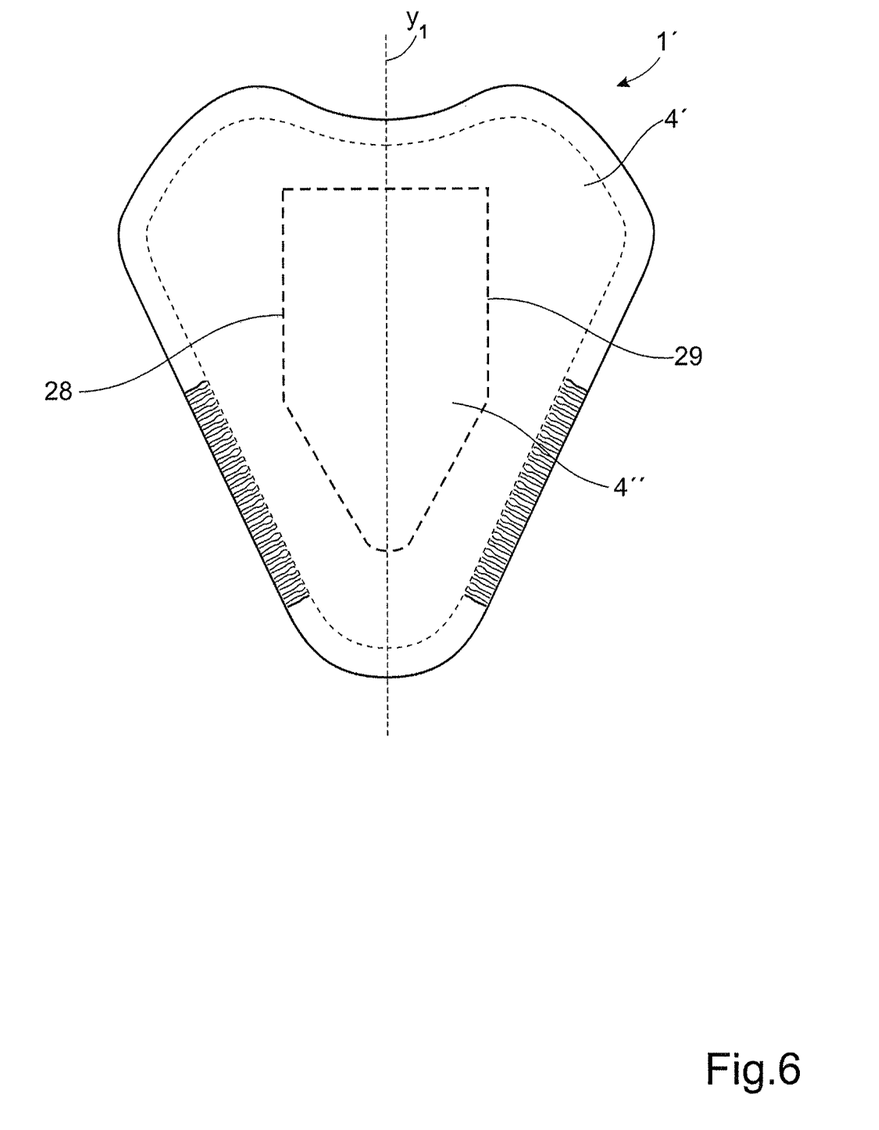
FIG. 6 shows a male incontinence guard according to a further embodiment of the invention.

FIG. 6 shows an embodiment of the invention in which two absorbent cores are used, i.e. a male incontinence guard 1' with an absorbent body which comprises a primary absorbent core 4' and a secondary absorbent core 4". In a manner which corresponds to FIG. 1, the incontinence guard 1' according to FIG. 6 is arranged along a longitudinal axis Y1. The primary absorbent core 4' corresponds generally to the absorbent core 4 described above with reference to FIGS. 1 and 2. Also, the remaining components of the incontinence guard 1' of FIG. 6 are also the same as the corresponding components of the embodiment in FIG. 1.

A difference between the embodiment of FIG. 6 and the embodiment of FIG. 1 is that the primary absorbent core 4' and the secondary absorbent core 4" shown in FIG. 6 are arranged in a stacked configuration. In an embodiment, this means that the secondary core 4" is preferably arranged on top of the primary core 4', i.e. so that the secondary core 4" is closest to the wearer's body during use of the incontinence guard 1'.

The embodiment according to FIG. 6 is particularly intended to simplify the above-mentioned manufacturing process, i.e. with regard to the folding procedure described with reference to FIGS. 3-5. To this end, the secondary absorbent core 4" is formed with side edges 28, 29 which at least partly generally parallel to the longitudinal axis Y1. Also, according to a further embodiment, the positions of the side edges 28, 29 correspond to the folding lines 22, 24 shown for example in FIG. 4 and being described above.

The invention is not limited to the embodiment but can be varied within the scope of the appended claims. For example, the particular shape of the incontinence guard 1 as shown in FIGS. 1 and 2 should not be considered as limiting the invention. Also, the shape of the guard 1 of the invention may be symmetrical about a transverse centre line through the article, as shown in FIG. 1, or may be asymmetrical with end portions having differing shapes and/or differing sizes.

Furthermore, the materials and dimensions used for the different layers forming the absorbent article 1 can be varied, as indicated above.

The invention claimed is:

1. A male incontinence guard comprising a fluid-impermeable backsheet, a fluid-permeable topsheet and an absorbent body arranged between said backsheet and said topsheet,
   wherein said topsheet faces the user when the incontinence guard is worn by said user, said guard having a longitudinal extension along a longitudinal axis (Y1) and a transverse extension along a transverse axis (X1), said transverse axis (X1) dividing said guard into an upper region and a lower region, wherein said transverse axis (X1) extends between a first lower corner point and a second lower corner point which define two outermost points of said guard between which said guard has a first width;

said upper region comprising an inwardly recessed curvature portion extending between a first upper corner point and a second upper corner point and having an arcuate shape, said upper corner points defining a second width (w2);

wherein the first width (w1) is greater than the second width (w2), and wherein said first lower corner point and first upper corner point and said second lower corner point and second upper corner point, respectively, are connected by outer side edges, and wherein said guard is arranged having elasticized elements arranged along outer edges of said lower region, and wherein the ratio between the first width (w1) and the second width (w2) is in the range of 30-80%, and wherein the ratio between a distance (d1) defined by an imaginary longitudinal line (Y2), being parallel to said longitudinal axis (Y1) and extending from any one of said upper corner points to said transversal axis (X1), and a distance (d2) extending from any one of said lower corner points to said longitudinal line (Y2), is in the range of 0.25-4.0, wherein a straight line is defined as extending through a lower corner point and an upper corner point, and wherein an angle (α) is defined between said straight line and said imaginary longitudinal line (Y2), said angle (α) being in the range of 12-78 degrees, and wherein a measurement (d4) is defined as a distance between said straight line and a maximum outer extension of said incontinence guard, wherein said measurement (d4) is less than 25% of a distance between first lower corner point and the first upper corner point; and wherein said inwardly recessed curvature portion defines an outer boundary edge extending between said upper corner points and wherein said outer boundary edge lies inwardly of an imaginary transverse line (X2) extending between said upper corner points.

2. The male incontinence guard according to claim 1, said guard being formed with a tapering shape as regarded from the lower corner points and along the lower region.

3. The male incontinence guard according to claim 1, wherein said outer boundary edge has a radius (r1) which is in the range of 60-1400 mm.

4. The male incontinence guard according to claim 1, wherein the ratio between the first width (w1) and the second width (w2) is in the range of 40-75%.

5. The male incontinence guard according to claim 1, wherein the first width (w1) is in the range of 110-280 mm.

6. The male incontinence guard according to claim 1, wherein the second width (w2) is in the range of 50-151 mm.

7. The male incontinence guard according to claim 1, wherein a maximum recess depth (d3) of said inwardly recessed curvature portion does not extend below said transversal axis (X1).

8. The male incontinence guard according to claim 7, wherein said maximum recess depth (d3) is the range of 2-30 mm.

9. The male incontinence guard according to claim 1, wherein said lower region of said guard comprises a lower edge having a convex arcuate shape with a radius (r2) defining a ratio of from 0.9 to 1.1 to said radius (r1) of said inwardly recessed curvature portion.

10. The male incontinence guard according to claim 1, wherein said outer side edges are generally straight.

11. The male incontinence guard according to claim 1, wherein said absorbent body has an outer edge which generally follows an outer edge of the guard and defines an edge region having a width which is generally equal along the entire outer edge of the guard.

12. The male incontinence guard according to claim 1, wherein said absorbent body comprises a primary absorbent core and a secondary absorbent core arranged in a stacked configuration.

13. The male incontinence guard according to claim 12, wherein said secondary core has an area in an XY plane which is smaller than an area of the primary core in the XY plane.

14. The male incontinence guard according to claim 13, wherein at least one of said primary core and said secondary core comprises superabsorbent material.

15. The male incontinence guard according to claim 14, wherein said superabsorbent material is a superabsorbent polymer.

16. The male incontinence guard according to claim 14, wherein said superabsorbent material is in the form of a foam.

17. The male incontinence guard according to claim 12, wherein the secondary core is formed with side edges being at least partly generally parallel to said longitudinal axis (Y1).

18. The male incontinence guard according to claim 1, wherein said elasticized elements are in the form of an elasticized film attached to said guard.

19. The male incontinence guard according to claim 1, wherein said elasticized elements are in the form of elastic threads attached to said guard.

20. The male incontinence guard according to claim 1, wherein said elasticized elements are in the form of an elastic foam attached to said guard.

21. The male incontinence guard according to claim 1, wherein said elasticized elements are in the form of an elastic laminate attached to said guard.

22. The male incontinence guard according to claim 1, wherein said elasticized elements extend up to said lower first and second corner points.

23. A package comprising a plurality of male incontinence guards according to claim 1, said male incontinence guards being individually wrapped and positioned in said package.

24. A method for manufacturing the male incontinence guard as defined in claim 1, having the longitudinal extension along the longitudinal axis (Y1) and the transverse extension along the transverse axis (X1), said transverse axis (X1) dividing said guard into the upper region and the lower region, said method comprising:
providing the fluid-impermeable backsheet;
providing the fluid-permeable topsheet; and
providing the absorbent body between said backsheet and said topsheet;
the method further comprising the following steps:
folding a first portion of the incontinence guard towards the centre of said incontinence guard;
folding a second portion of the incontinence guard towards the centre of said incontinence guard so that it at least partly covers the first portion; and
folding a bottom portion of the incontinence guard upwards so as to partly cover both the first portion and the second portion.

25. The method according to claim 24, wherein said bottom portion is folded while forming a distance (d5)

between a top edge of the incontinence guard and an upper edge of the bottom portion of the incontinence guard, said distance (d5) being up to 30 mm.

26. The method according to claim 24, further comprising:
   individually wrapping the male incontinence guard; and
   positioning the individually wrapped male incontinence guard, with other individually wrapped male incontinence guards, in a package.

* * * * *